(12) United States Patent
DiCarlo

(10) Patent No.: US 7,959,631 B2
(45) Date of Patent: *Jun. 14, 2011

(54) ABLATION DEVICE WITH COMPRESSION BALLOON

(75) Inventor: Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/721,430

(22) Filed: Mar. 10, 2010

(65) Prior Publication Data

US 2010/0168734 A1    Jul. 1, 2010

Related U.S. Application Data

(63) Continuation of application No. 11/315,426, filed on Dec. 21, 2005, now Pat. No. 7,704,248.

(51) Int. Cl.
*A61B 18/14* (2006.01)

(52) U.S. Cl. ......................................... 606/41

(58) Field of Classification Search ...................... 606/41
See application file for complete search history.

(56) References Cited

U.S. PATENT DOCUMENTS

| 3,174,851 | A | 3/1965 | Buebler et al. |
| 3,351,463 | A | 11/1967 | Rozner et al. |
| 3,753,700 | A | 8/1973 | Harrison et al. |
| 4,823,812 | A | 4/1989 | Eshel et al. |
| 5,672,153 | A | 9/1997 | Lax et al. |
| 5,846,239 | A | 12/1998 | Swanson et al. |
| 5,855,576 | A | 1/1999 | LeVeen et al. |
| 5,925,038 | A | 7/1999 | Panescu et al. |
| 5,957,919 | A | 9/1999 | Laufer |
| 6,004,269 | A | 12/1999 | Crowley et al. |
| 6,053,937 | A | 4/2000 | Edwards et al. |

(Continued)

FOREIGN PATENT DOCUMENTS

DE    3402573 A1    8/1985

(Continued)

OTHER PUBLICATIONS

International Preliminary Report on Patentability (Chapter I of the Patent Cooperation Treaty) from The International Bureau for the related International Application No. PCT/US2006/062030 dated Jul. 3, 2008 (7 pages).

(Continued)

*Primary Examiner* — Lee S Cohen
(74) *Attorney, Agent, or Firm* — Vista IP Law Group LLP

(57) ABSTRACT

A tissue ablation device includes an array of elongate electrodes configured to be deployed in tissue, wherein the deployed electrode array defines a tissue ablation region, an inflatable balloon configured to be deployed in tissue, and a coupler securing the balloon relative to the one or more elongate electrodes, wherein the balloon, when inflated, is configured to apply a force to tissue located in the tissue ablation region. An ablation device includes a first array of electrodes, a second array of electrodes, a first inflatable balloon, and a coupler securing the first balloon relative to the first and second electrode arrays. A method of ablating tissue includes positioning an array of elongate electrodes and an inflatable balloon proximate tissue to be ablated, inflating the balloon to compress a tissue region located between the balloon and the electrode array, and energizing the electrode array to ablate the tissue region.

15 Claims, 5 Drawing Sheets

U.S. PATENT DOCUMENTS

| | | | |
|---|---|---|---|
| 6,077,257 A | 6/2000 | Edwards et al. | |
| 6,208,893 B1 | 3/2001 | Hofmann | |
| 6,454,766 B1 | 9/2002 | Swanson et al. | |
| 6,726,694 B2 | 4/2004 | Blatter et al. | |
| 6,780,183 B2 | 8/2004 | Jimenez, Jr. et al. | |
| 7,704,248 B2 * | 4/2010 | DiCarlo | 606/41 |
| 2002/0042564 A1 | 4/2002 | Cooper et al. | |
| 2002/0068932 A1 | 6/2002 | Edwards et al. | |
| 2002/0120261 A1 | 8/2002 | Morris et al. | |
| 2003/0018327 A1 | 1/2003 | Truckai et al. | |
| 2003/0060817 A1 | 3/2003 | Sauvageau et al. | |
| 2003/0060856 A1 | 3/2003 | Chornenky et al. | |
| 2004/0073238 A1 | 4/2004 | Makower | |
| 2004/0181216 A1 | 9/2004 | Kelly et al. | |
| 2004/0243122 A1 | 12/2004 | Auth et al. | |
| 2004/0267256 A1 | 12/2004 | Garabedian et al. | |
| 2005/0010203 A1 | 1/2005 | Edwards et al. | |

FOREIGN PATENT DOCUMENTS

| | | |
|---|---|---|
| DE | 4007295 | 12/1991 |
| EP | 1169972 A1 | 1/2002 |
| WO | WO 91/17714 | 11/1991 |
| WO | WO 92/10142 | 6/1992 |
| WO | WO 96/07360 | 3/1996 |
| WO | WO 99/42043 | 8/1999 |
| WO | WO 99/62413 | 12/1999 |
| WO | WO 00/09208 | 2/2000 |
| WO | WO 03/034932 | 5/2003 |
| WO | WO 2005/003007 A1 | 4/2005 |

OTHER PUBLICATIONS

PCT International Search Report for PCT/US2006/062030, Applicant: Boston Scientific Scimed, Inc., Form PCT/ISA/210 and 220, dated Sep. 4, 2007 (6 pages).

PCT Written Opinion of the International Search Authority for PCT/US2006/062030, Applicant: Boston Scientific Scimed, Inc., Form PCT/ISA/210 and 220, dated Sep. 4, 2007 (6 pages).

Matt Brenner, "Innovative Approaches to Lung Volume Reduction for Emphysema", www.chestjournal.com, Jul. 1, 2004, pp. 238-248.

MedTech1.com Medical Technology Affecting Our Lives., "Percutaneous Radiofrequency Ablation of Lung Tumors Using RITA Medical Systems Products shown safe and Effective in Multicarrier Prospective Clinical Trail", Dec. 5, 2003 (1 page).

* cited by examiner

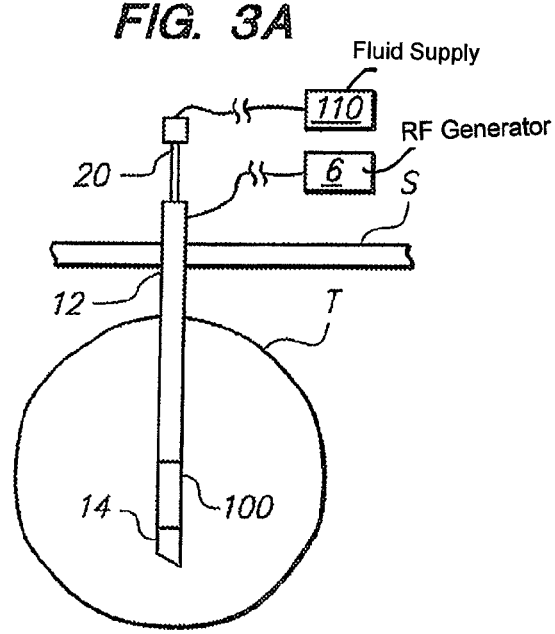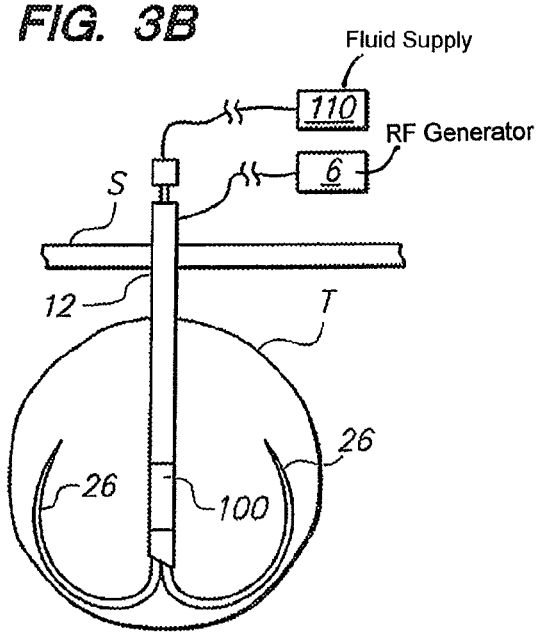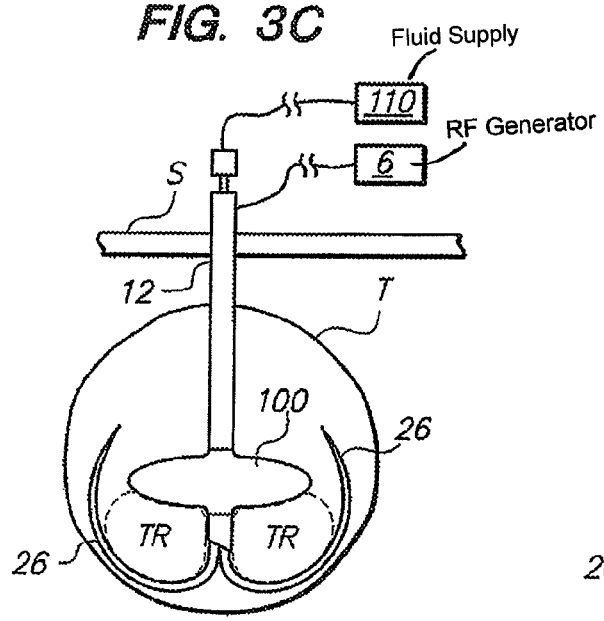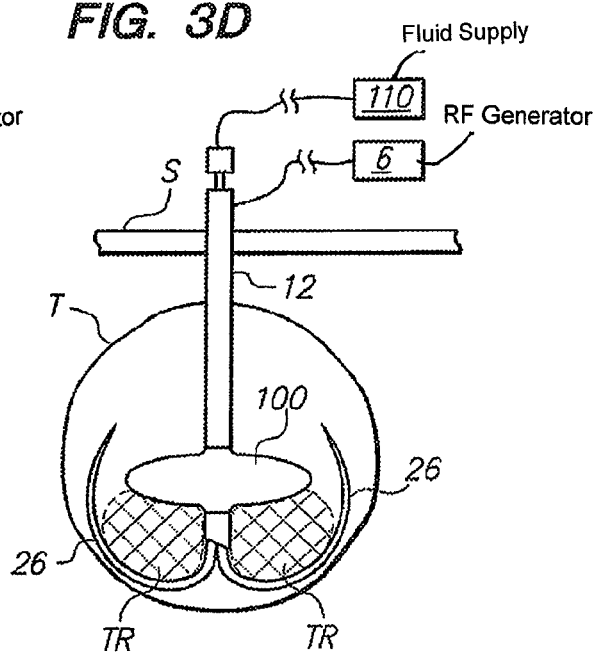

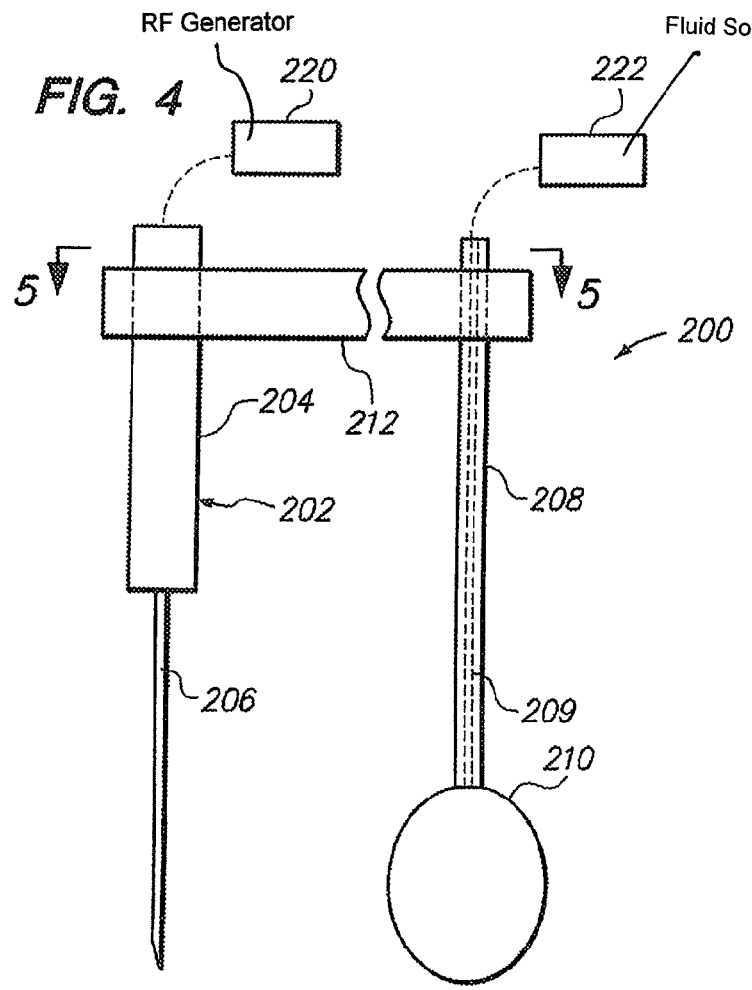
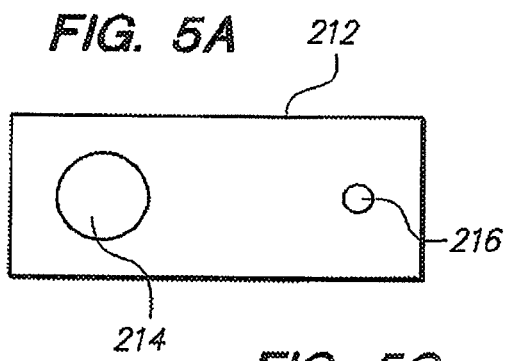
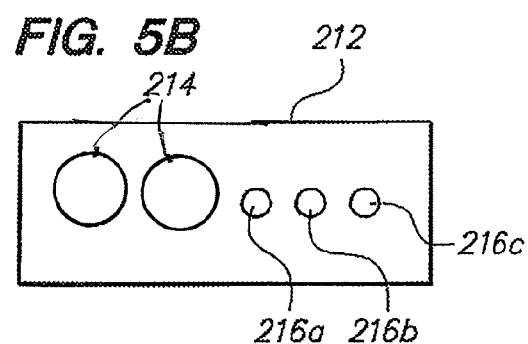
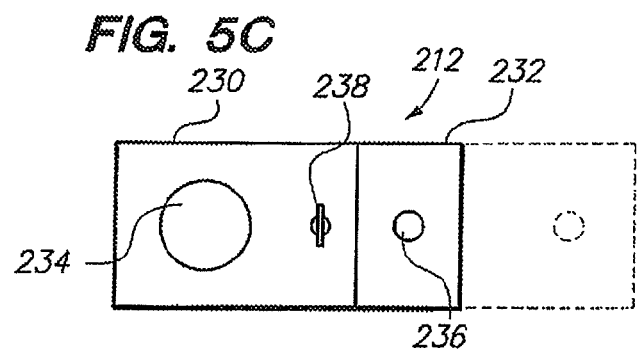

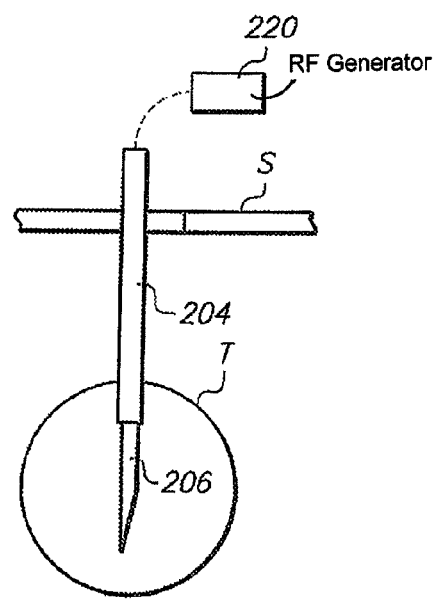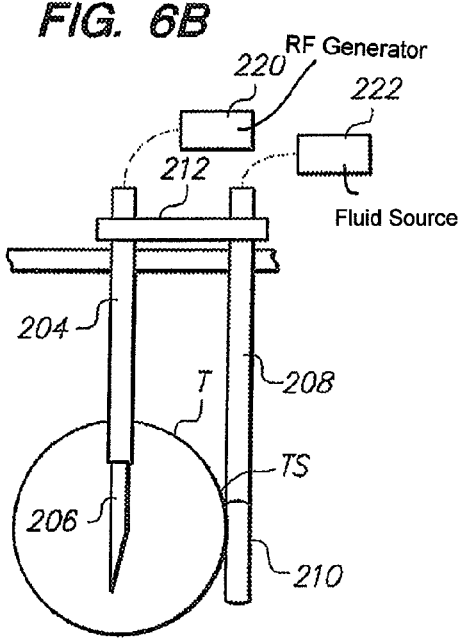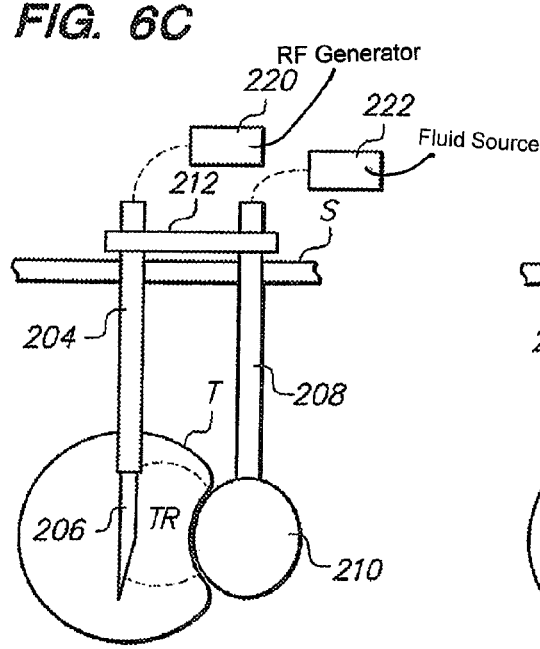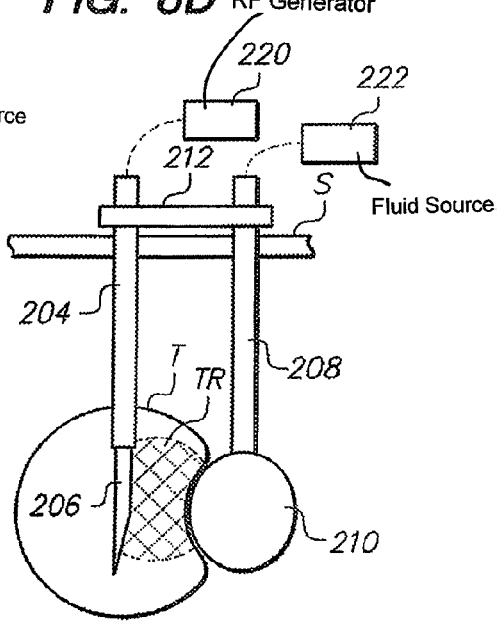

ABLATION DEVICE WITH COMPRESSION BALLOON

CROSS REFERENCE TO RELATED APPLICATIONS

This application is a continuation of U.S. application Ser. No. 11/315,426, filed Dec. 21, 2005, now issued as U.S. Pat. No. 7,704,248, the disclosure of which is hereby incorporated by reference.

FIELD

The field of the invention relates generally to radio frequency (RF) devices for the treatment of tissue, and more particularly, to electrosurgical devices having multiple tissue-penetrating electrodes that are deployed in an array to treat volumes of tissue.

BACKGROUND

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction. In particular, radio frequency ablation (RFA) may be used to treat patients with tissue anomalies, such as liver anomalies and many primary cancers, such as cancers of the stomach, bowel, pancreas, kidney and lung. RFA treatment involves destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of electrode tines deployable from a cannula. Each of the tines includes a proximal end that is coupled to a generator, and a distal end that may project from a distal end of the cannula. The tines are arranged in an array with the distal ends located generally radially and uniformly spaced apart from the distal end of the cannula. The tines may be energized in a bipolar mode (i.e., current flows between closely spaced electrode tines) or a monopolar mode (i.e., current flows between one or more electrode tines and a larger, remotely located common electrode) to heat and necrose tissue within a precisely defined volumetric region of target tissue. To assure that the target tissue is adequately treated and/or to limit damaging adjacent healthy tissues, the array of tines may be arranged uniformly, e.g., substantially evenly and symmetrically spaced-apart so that heat is generated uniformly within the desired target tissue volume.

When using heat to kill tissue at a target site, the effective rate of tissue ablation is highly dependent on how much of the target tissue is heated to a therapeutic level. In certain situations, complete ablation of target tissue that is adjacent a vessel may be difficult or impossible to perform, since significant bloodflow may draw the produced heat away from the vessel wall, resulting in incomplete necrosis of the tissue surrounding the vessel. This phenomenon, which causes the tissue with greater blood flow to be heated less, and the tissue with lesser blood flow to be heated more, is known as the "heat sink" effect. It is believed that the heat sink effect is more pronounced for ablation of tissue adjacent large vessels that are more than 3 millimeters (mm) in diameter. Due to the increased vascularity of certain tissue, such as liver tissue and lung tissue, the heat sink effect may cause recurrence of tumors after a radio frequency ablation.

SUMMARY

In accordance with some embodiments, a tissue ablation device includes an array of elongate electrodes configured to be deployed in tissue, wherein the deployed electrode array defines a tissue ablation region, an inflatable balloon configured to be deployed in tissue, and a coupler securing the balloon relative to the one or more elongate electrodes, wherein the balloon, when inflated, is configured to apply a force to tissue located in the tissue ablation region.

In accordance with other embodiments, an ablation device includes a first array of electrodes, a second array of electrodes, a first inflatable balloon, and a coupler securing the first balloon relative to the first and second electrode arrays.

In accordance with other embodiments, a method of ablating tissue includes positioning an array of elongate electrodes and an inflatable balloon proximate tissue to be ablated, inflating the balloon to compress a tissue region located between the balloon and the electrode array, and energizing the electrode array to ablate the tissue region.

Other and further aspects and features will be evident from reading the following detailed description of the embodiments.

BRIEF DESCRIPTION OF THE DRAWINGS

The drawings illustrate the design and utility of embodiments. It should be noted that the figures are not drawn to scale and that elements of similar structures or functions are represented by like reference numerals throughout the figures. In order to better appreciate how the advantages and objects of the embodiments are obtained, a more particular description of the embodiments will be rendered by reference to the accompanying drawings. These drawings depict only typical embodiments and are not therefore to be considered limiting in the scope of the claimed invention.

FIGS. 3A-3D are cross-sectional views, showing a method for treating tissue using the system of FIG. 1A, in accordance with some embodiments;

FIG. 4 is a schematic diagram of a tissue ablation system in accordance with other embodiments;

FIG. 5A illustrates a coupler in accordance with some embodiments;

FIG. 5B illustrates a coupler in accordance with other embodiments;

FIG. 5C illustrates a coupler in accordance with other embodiments;

FIGS. 6A-6D are cross-sectional views, showing a method for treating tissue using the system of FIG. 4, in accordance with some embodiments;

DETAILED DESCRIPTION OF THE EMBODIMENTS

Figure 1A:
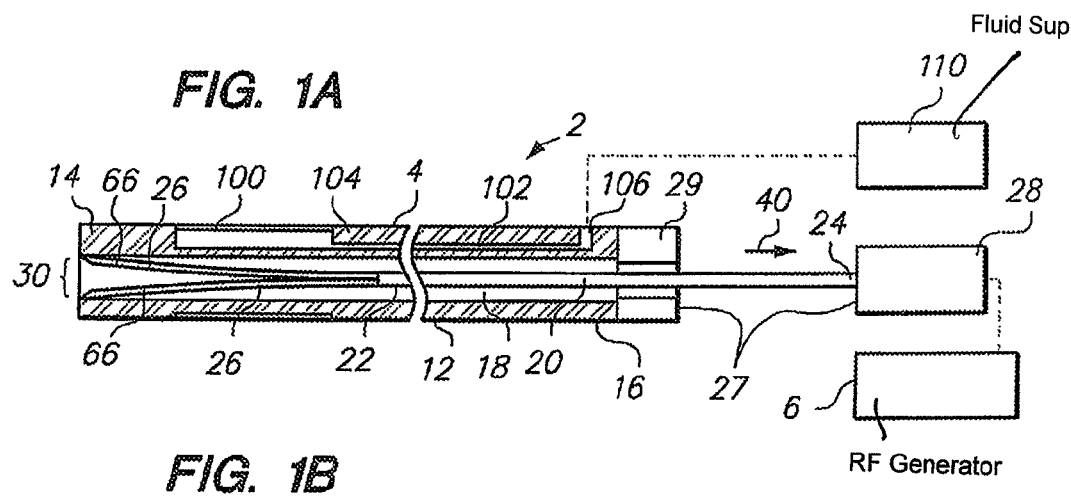
FIG. 1A is a schematic diagram of a tissue ablation system in accordance with some embodiments, showing the device having electrodes and an inflatable balloon.

FIG. 1A illustrates a tissue ablation system 2 in accordance with some embodiments. The tissue ablation system 2 includes a probe assembly 4 configured for introduction into the body of a patient for ablative treatment of target tissue, and a radio frequency (RF) generator 6 configured for supplying RF energy to the probe assembly 4 in a controlled manner.

The probe assembly 4 also includes an elongate tube 12, a shaft 20 slidably disposed within the tube 12, and an array 30 of electrodes 26 carried by the shaft 20. The tube 12 has a distal end 14, a proximal end 16, and a central lumen 18 extending through the tube 12 between the distal end 14 and the proximal end 16. The tube 12 may be rigid, semi-rigid, or flexible depending upon the designed means for introducing the tube 12 to the target tissue. The tube 12 is composed of a suitable material, such as plastic, metal or the like, and has a suitable length, typically in the range from 5 cm to 30 cm, preferably from 10 cm to 20 cm. The length of the tube 12 can also have other dimensions. If composed of an electrically conductive material, the tube 12 is preferably covered with an insulative material. The tube 12 has an outside cross sectional dimension consistent with its intended use, typically being from 0.5 mm to 5 mm, usually from 1.3 mm to 4 mm. The tube 12 may have an inner cross sectional dimension in the range from 0.3 mm to 4 mm, preferably from 1 mm to 3.5 mm. The tube 12 can also have other outside and inner cross sectional dimensions in other embodiments.

Figure 1B:
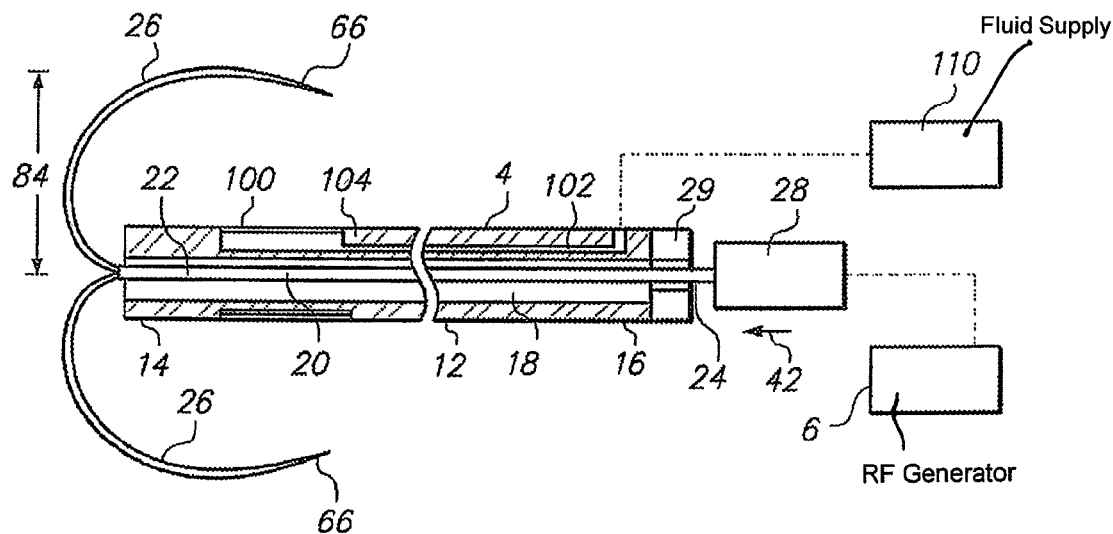
FIG. 1B illustrates the system of FIG. 1A, showing the electrodes being deployed.

It can be appreciated that longitudinal translation of the shaft 20 relative to the tube 12 in a proximal direction 40 retracts the electrodes 26 into the distal end 14 of the tube 12 (FIG. 1A), and longitudinal translation of the shaft 20 relative to the tube 12 in a distal direction 42 deploys the electrodes 26 from the distal end 14 of the tube 12 (FIG. 1B). The shaft 20 comprises a distal end 22 and a proximal end 24. Like the tube 12, the shaft 20 is composed of a suitable material, such as plastic, metal or the like.

In the illustrated embodiment, each electrode 26 takes the form of an electrode tine, which resembles the shape of a needle or wire. Each of the electrodes 26 is in the form of a small diameter metal element, which can penetrate into tissue as it is advanced from a target site within the target region. In some embodiments, distal ends 66 of the electrodes 26 may be honed or sharpened to facilitate their ability to penetrate tissue. The distal ends 66 of these electrodes 26 may be hardened using conventional heat treatment or other metallurgical processes. They may be partially covered with insulation, although they will be at least partially free from insulation over their distal portions.

When deployed from the tube 12, the array 30 of electrodes 26 has a deployed configuration that defines a volume having a periphery with a radius 84 in the range from 0.5 to 4 cm. However, in other embodiments, the maximum radius can be other values. The electrodes 26 are resilient and pre-shaped to assume a desired configuration when advanced into tissue. In the illustrated embodiments, the electrodes 26 diverge radially outwardly from the tube 12 in a uniform pattern, i.e., with the spacing between adjacent electrodes 26 diverging in a substantially uniform and/or symmetric pattern.

In the illustrated embodiments, each electrode 26 has a flared curvilinear profile that resembles a portion of a parabola. Particularly, when the electrodes 26 are deployed, the electrodes 26 each extends proximally, and then everts distally, such that each electrode 26 forms a profile that resembles at least a portion of a parabola. As shown in FIG. 1B, the deployed electrode 26 is located at the distal end 14 of the cannula, and each deployed electrode 26 has a distal end that points at least partially towards a proximal direction. It should be noted that the electrodes 26 should not be limited to the profiles shown in FIG. 1B, and that in alternative embodiments, the electrodes 26 can have different deployed profiles. For examples, in other embodiments, each of the electrodes 26 can each have a flared deployed profile, a substantially rectilinear deployed profile, a deployed profile that resembles a 90° bent, or a deployed profile that resembles a portion (e.g., a quarter) of a circle or an ellipse.

It should be noted that although a total of two electrodes 26 are illustrated in FIG. 1B, in other embodiments, the probe assembly 4 can have more or fewer than two electrodes 26. In exemplary embodiments, pairs of adjacent electrodes 26 can be spaced from each other in similar or identical, repeated patterns and can be symmetrically positioned about an axis of the shaft 20. It will be appreciated that a wide variety of particular patterns can be provided to uniformly cover the region to be treated. In other embodiments, the electrodes 26 may be spaced from each other in a non-uniform pattern.

The electrodes 26 can be made from a variety of electrically conductive elastic materials. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The electrodes 26 may also be made from any of a wide variety of stainless steels. The electrodes 26 may also include the Platinum Group metals, especially platinum, rhodium, palladium, rhenium, as well as tungsten, gold, silver, tantalum, and alloys of these metals. These metals are largely biologically inert. They also have significant radiopacity to allow the electrodes 26 to be visualized in-situ, and their alloys may be tailored to accomplish an appropriate blend of flexibility and stiffness. They may be coated onto the electrodes 26 or be mixed with another material used for construction of the electrodes 26.

In the illustrated embodiments, RF current is delivered to the electrode array 30 in a monopolar fashion, which means that current will pass from the electrode array 30, which is configured to concentrate the energy flux in order to have an injurious effect on the surrounding tissue, to a dispersive electrode (not shown), which is located remotely from the electrode array 30 and has a sufficiently large area (typically 130 $cm^2$ for an adult), so that the current density is low and non-injurious to surrounding tissue. The dispersive electrode may be attached externally to the patient, e.g., using a contact pad placed on the patient's skin. In other embodiments, RF energy may be delivered in a bipolar fashion in that energy is delivered from one electrode(s) 26 to another electrode(s) 26 on the array 30.

Figure 2:
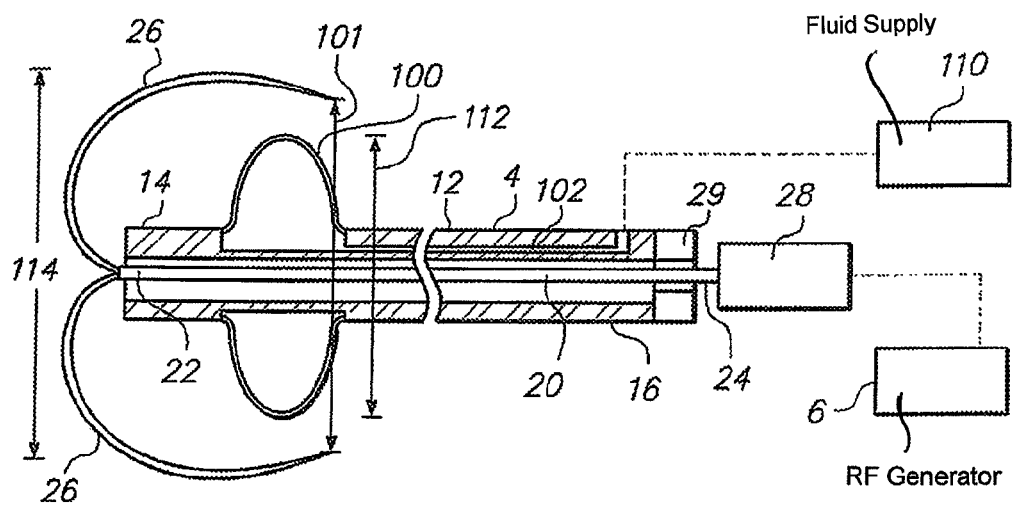
FIG. 2 illustrates the system of FIG. 1A, showing the balloon being inflated.

As shown in FIG. 1A, the probe assembly 4 also includes an inflatable balloon 100 secured to the tube 12. The balloon 100 is used to compress tissue between the balloon 100 (when inflated) and the array 30 of electrodes 26 during use. The tube 12 includes a fluid delivery channel 102 within a wall 104 of the tube 12, and a port 106 in fluid communication with the fluid delivery channel 102, wherein the fluid delivery channel 102 is used for delivering inflation fluid to the balloon 100. During use, a fluid supply 110 is coupled to the port 106 (e.g., via a tube), and inflation fluid (gas or liquid) is delivered from the fluid supply 110 to the balloon 100 via the fluid delivery channel 102, thereby inflating the balloon 100 (FIG. 2). The inflated balloon 100 can have different inflated shapes in different embodiments. For examples, the inflated balloon 100 can have a circular profile, an elliptical profile, a triangular profile, or other customized profiles. In some embodiments, the inflated balloon 100 has a cross sectional dimension 112 which is between 50% of a cross sectional dimension 114 of the deployed array 30 and 150% of the cross sectional dimension 114 of the deployed array 30. For example, the balloon 100, when inflated, can have a cross sectional dimension 112 that is larger than the cross sectional dimension 114 of the deployed array 30. In such cases, the balloon 100 can be located proximal to the tips of the electrodes 26 so that the tips do not puncture the balloon 100 when inflated. In other embodiments, the inflated balloon 100 has a cross sectional dimension 112 that is smaller than an opening 101 defined by the distal ends 66 of the electrodes 26, thereby allowing the balloon 100 to be positioned at least partially within the opening 101 without being punctured by the electrodes 26. In other embodiments, the inflated balloon 100 can have other cross sectional dimensions 112 different from those discussed previously. The balloon 100 can be made from a variety of materials, such as a polymer or latex.

In some embodiments, at least a portion of the balloon 100 can include electrically conductive material, thereby allowing the balloon 100 to function as an electrode. For example, the balloon 100 can have one or more regions made from a metal, or covered with metal dusts. Electrically conductive balloons have been described in U.S. Pat. Nos. 5,846,239, 6,454,766, and 5,925038, the entire disclosures of which are expressly incorporated by reference herein. One or more electrical wires (e.g., housed within the wall 104 of the tube 12) may be used to deliver electrical energy from the RF generator 6 to the balloon 100. In such cases, the array 30 of electrodes 26 and the balloon 100 are used to deliver RF current in a bipolar fashion, which means that current will pass between the array 30 of electrodes 26 and the balloon 100. In a bipolar arrangement, the array 30 and the balloon 100 will be insulated from each other in any region(s) where they would or could be in contact with each other during a power delivery phase. If the tube 12 is made from an electrically conductive material, an insulator (not shown) can be provided to electrically insulate the operative balloon 100 from the electrodes 26 in the array 30.

Returning to FIGS. 1A and 1B, the probe assembly 4 further includes a handle assembly 27, which includes a handle portion 28 mounted to the proximal end 24 of the shaft 20, and a handle body 29 mounted to the proximal end 16 of the tube 12. The handle portion 28 is slidably engaged with the handle body 29 (and the tube 12). The handle portion 28 and the handle body 29 can be composed of any suitable rigid material, such as, e.g., metal, plastic, or the like.

The handle portion 28 also includes electrical connector(s) (not shown), which allows the electrode array 30 of the probe assembly 4 to be connected directly or indirectly (e.g., via a conductor) to the generator 6 during use. The RF generator 6 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., which markets these power supplies under the trademarks RF2000 (100 W) and RF3000 (200 W). In other embodiments, generators having other ranges of operating frequency or ranges of voltage can also be used. Other general purpose electrosurgical power supplies can also be used in other embodiments.

Referring now to FIGS. 3A-3D, the operation of the tissue ablation system 2 is described in treating a treatment region within tissue T located beneath the skin S of a patient. The tissue T can be at least a portion of, a lung tissue, a liver tissue, or other tissue within a body.

The tube 12 is first introduced within a treatment region, so that the distal end 14 of the tube 12 is located at a target site, as shown in FIG. 3A. This can be accomplished using any one of a variety of techniques. In some cases, the tube 12 and shaft 20 may be introduced to the target site TS percutaneously directly through the patient's skin or through an open surgical incision. In this case, the tube 12 (or the electrode 26) may have a sharpened tip, e.g., in the form of a needle, to facilitate introduction to the target site. In such cases, it is desirable that the tube 12 be sufficiently rigid, i.e., have a sufficient column strength, so that it can be accurately advanced through tissue T. In other cases, the tube 12 may be introduced using an internal stylet that is subsequently exchanged for the shaft 20 and electrode array 30. In this latter case, the tube 12 can be relatively flexible, since the initial column strength will be provided by the stylet. More alternatively, a component or element may be provided for introducing the tube 12 to the target site. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The tube 12 and shaft 20 can then be introduced through the sheath lumen, so that the distal end 14 of the tube 12 advances from the sheath to the target site.

After the tube 12 is properly placed, the electrode array 30 is deployed out of the lumen 18 of the tube 12, as shown in FIG. 3B.

Next, inflation fluid is delivered from the fluid source 110 to inflate the balloon 100, thereby compressing the tissue region TR that is between the balloon 100 and the electrodes 26 (FIG. 3C). In some embodiments, the size of the balloon 100 can be adjusted (e.g., by varying the amount of inflation fluid that is delivered into the balloon 100) to thereby change a degree of compression of the tissue region TR. For example, an increase in the amount of inflation fluid delivered to the balloon 100 will cause the balloon 100 to increase in size, thereby increasing the amount of compression created on the tissue region TR, and vice versa. In other embodiments, the amount of compression on the tissue region TR can be adjusted by positioning the balloon 100 relative to the deployed electrodes 26. For example, the tube 12 can be positioned relative to the shaft 20 to vary a distance between the balloon 100 and the electrodes 26, thereby changing an amount of compression on the tissue region TR.

Next, with the RF generator 6 connected to the probe assembly 4, the RF generator 6 is operated to deliver ablation energy to the electrodes 26 either in a monopolar mode or a bipolar mode. While ablation energy is being delivered, compression of the tissue region TR between the balloon 100 and the electrodes 26 is maintained. The compression on the tissue region TR reduces blood flow to the tissue region TR, thereby preventing or reducing heat from being carried away by blood flow, which in turn, improves a tissue ablation rate. After a desired amount of ablation energy has been delivered, the treatment region TR is necrosed, thereby creating a lesion on the treatment region TR (FIG. 3D).

In many cases, a single ablation may be sufficient to create a desired lesion. However, if it is desired to perform further ablation to increase the lesion size or to create lesions at different site(s), the electrodes 26 may be introduced and deployed at different target site(s), and the same steps discussed previously may be repeated. When desired lesions have been created, the electrodes 26 are retracted into the lumen 18 of the tube 12, and the probe assembly 4 is removed from the patient.

In other embodiments, instead of placing the balloon 100 within tissue T, the balloon 100 can be placed next to a periphery of the tissue, such as, at a surface of the tissue. In such cases, after deploying the electrodes 26 within the tissue T, the tube 12 can be retracted proximally until the balloon 100 is outside the tissue T. The balloon 100 is then inflated to press against a surface of the tissue T, thereby compressing tissue region that is within tissue T.

In the above embodiments, the relative position between the balloon 100 and the array 30 of electrodes 26 is established using the tube 12 and the shaft 20. In other embodiments, the relative position between the balloon 100 and electrode(s) 26 may be established using other structures. Also, in further embodiments, the balloon 100 needs not be located on the tube 12 that carries the electrodes 26. Instead, the balloon 100 can be carried by a separate structure.

FIG. 4 illustrates an ablation system 200 in accordance with other embodiments. The ablation system 200 includes an ablation device 202 having one or more electrodes 206 and a structure 204 for carrying the electrode(s) 206, a balloon 210, a shaft 208 for carrying the balloon 210, and a coupler 212 for establishing a relative position between the balloon 210 and the electrode(s) 206. The electrode(s) 206 each has a rectilinear profile, but can have other shapes in other embodiments. In some embodiments, the ablation device 202 includes one electrode 206. In other embodiments, the ablation device 202 includes a plurality of electrodes 206. For examples, the electrodes 206 can be arranged in a row, multiple rows, or in other customized patterns. The ablation system 200 also includes a RF generator 220 for providing RF energy to the electrode(s) 206 (e.g., in a monopolar or bipolar fashion), and a fluid source 222 for delivering inflation fluid (gas or liquid) to inflate the balloon 210. The shaft 208 includes a fluid delivery channel 209 for delivering fluid from the fluid source 222 to the balloon 210. In some embodiments, the balloon 210 can include one or more conductive regions, thereby allowing the balloon 210 to function as an electrode. In such cases, the balloon 210 is electrically connected to the generator 220 during use.

FIG. 5A illustrates a top view of the coupler 212 of FIG. 4 in accordance with some embodiments. The coupler 212 includes a first opening 214 sized to mate with the structure 204 of the ablation device 202, and a second opening 216 sized to mate with the shaft 208. In the illustrated embodiments, the coupler 212 is detachably coupled to the structure 204 and the shaft 208. In other embodiments, the coupler 212 is permanently secured (e.g., via a glue or a suitable adhesive) to the structure 204, the shaft 208, or both.

FIG. 5B illustrates a top view of the coupler 212 of FIG. 4 in accordance with other embodiments. The coupler 212 includes a plurality of second openings 216a-216c, each of which is sized to mate with the shaft 208. Such configuration allows a distance between the balloon 210 and the electrode(s) 206 be adjusted by selectively mating the shaft 208 to a desired one of the openings 216a-216c. In other embodiments, instead of, or in addition to, the plurality of second openings 216a-216c, the coupler 212 can include a plurality of first openings 214, thereby allowing the structure 204 to be secured to different portion of the coupler 212.

FIG. 5C illustrates a top view of the coupler 212 of FIG. 4 in accordance with other embodiments. The coupler 212 includes a first portion 230 and a second portion 232 that is moveable relative to the first portion 230. The first portion 230 includes a first opening 234 sized to mate with the structure 204 of the ablation device 202, and the second portion 232 includes a second opening 236 sized to mate with the shaft 208. In the illustrated embodiments, the coupler 212 is detachably coupled to the structure 204 and the shaft 208. In other embodiments, the coupler 212 is permanently secured (e.g., via a glue or a suitable adhesive) to the structure 204, the shaft 208, or both. During use, the second portion 232 can be translated relative to the first portion 230, thereby allowing a distance between the openings 234, 236 be adjusted. This, in turn, allows adjustment of a spacing between the balloon 210 and the electrode(s) 206. A securing device, such as a screw 238, can be provided to secure the second portion 232 relative to the first portion 230 after a desired spacing between the openings 234, 236 is obtained.

In the above embodiments, the opening 214 is sized such that it provides a frictional contact against a surface of the structure 204 when the structure 204 is inserted within the opening 214, thereby allowing the coupler 212 to be secured to the structure 204 via friction. Similarly, the opening 216 is sized such that it provides a frictional contact against a surface of the shaft 208 when the shaft 208 is inserted within the opening 216, thereby allowing the coupler 212 to be secured to the shaft 208. In other embodiments, the coupler 212 can be detachably secured to the structure 204 and/or the shaft 208 by other techniques. For example, the coupler 212 can include one or more screws, one or more snap-fit connections, or one or more pins for detachably securing itself to the structure 204 and/or the shaft 208. Also, in other embodiments, instead of the shafts 208, the opening 216 can be sized to mate with another structure that is used to carry (or is coupled to) the balloon 210. In addition, in other embodiments, the coupler 212 can have other shapes and configurations as long as the coupler 212 is capable of establishing a relative position between the electrode(s) 206 and the balloon 210.

Referring now to FIGS. 6A-6D, the operation of the tissue ablation system 200 is described in treating a treatment region TR within tissue T located beneath the skin S of a patient. First, an incision is made at the patient's skin S to thereby create an opening, and the electrodes 206 carried by the structure 204 are inserted through the opening (FIG. 6A). The electrodes 206 are advanced to penetrate the tissue T beneath the skin S, and are positioned until they are placed at a desired location. The tissue T can be at least a portion of, a lung tissue, a liver tissue, or other tissue within a body.

Next, the balloon 210 is inserted through the skin S, and the coupler 212 is detachably secured to the structure 204 and the shaft 208 that carries the balloon 210, thereby establishing a relative position between the balloon 210 and the electrodes 206 (FIG. 6B). Alternatively, if the coupler 212 is permanently secured to the structure 204, then the coupler 212 is detachably secured to the shaft 208 and not to the structure 204. In other embodiments, if the coupler 212 is permanently secured to the shaft 208, then the coupler 212 is detachably secured to the structure 204 and not to the shaft 208. As shown in the figure, the balloon 210, in its non-inflated state, is positioned next to a tissue surface TS.

Next, inflation fluid is delivered from the fluid source 222 to inflate the balloon 210, thereby compressing the tissue region TR that is between the balloon 210 and the electrodes 206 (FIG. 6C). In some embodiments, the size of the balloon 210 can be adjusted (e.g., by varying the amount of inflation fluid that is delivered into the balloon 210) to thereby change a degree of compression of the tissue region. For example, an increase in the amount of inflation fluid delivered to the balloon 210 will cause the balloon 210 to increase in size, thereby increasing the amount of compression created on the tissue region TR, and vice versa.

When the tissue region TR is desirably compressed, the RF generator 220 is operated to deliver ablation energy to the electrodes 206 either in a monopolar mode or a bipolar mode. The compression on the tissue reduces blood flow to the tissue, thereby preventing or reducing heat from being carried away by blood flow, which in turn, improves a tissue ablation rate. After a desired amount of ablation energy has been delivered, the tissue region TR is necrosed, thereby creating a lesion at the tissue region TR (FIG. 6D). In some embodiments, while ablation energy is being delivered, the degree of compression at the tissue region can be varied (e.g., by delivering additional inflation fluid to, or by removing delivered inflation fluid from, the balloon 210).

In many cases, a single ablation may be sufficient to create a desired lesion. However, if it is desired to perform further ablation to increase the lesion size or to create lesions at different site(s) within the same tissue T or elsewhere, the electrodes 206 may be introduced and deployed at different target site(s), and the same steps discussed previously may be repeated. When all desired lesions have been created, the electrodes 206 and the balloon 210 are removed from the patient.

Figure 7:
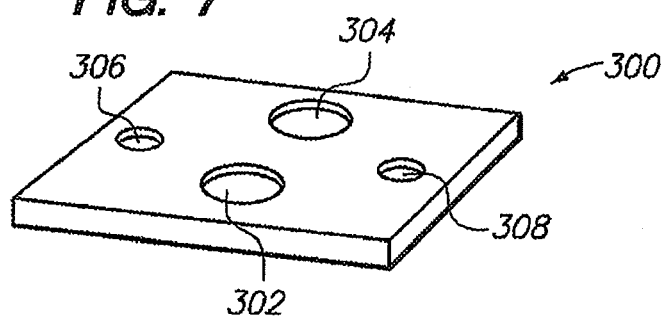
FIG. 7 illustrates a perspective view of a coupler in accordance with other embodiments.
Figure 8:
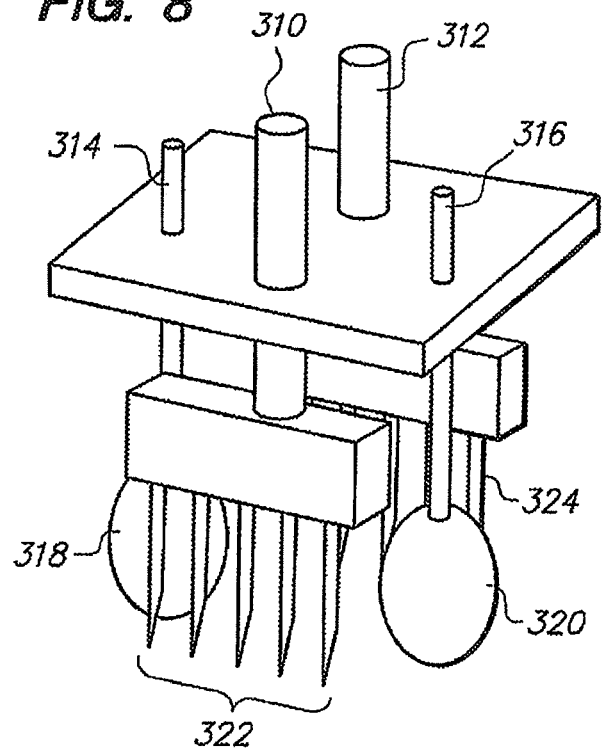
FIG. 8 illustrates an ablation system that uses the coupler of FIG. 7 in accordance with some embodiments.
Figure 9:
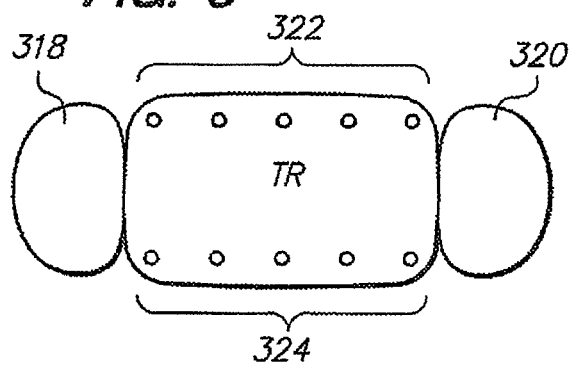
FIG. 9 illustrates an end view of a tissue being treated by the system of FIG. 8 in accordance with some embodiments.

In the above embodiments, the coupler 212 is configured to secure a relative position between the balloon 210 and the electrode(s) 206. In other embodiments, the coupler 212 can be configured to secure relative positions among two or more balloons and the electrode(s) 206, or among the balloon 210 with two or more sets of electrode(s) 206. FIG. 7 illustrates a coupler 300 in accordance with other embodiments. The coupler 300 includes a first opening 302 sized to mate with a first structure 310 that carries a first set of electrodes 322, a second opening 304 sized to mate with a second structure 312 that carries a second set of electrodes 324, a third opening 306 sized to mate with a first shaft 314 that carries a first balloon 318, and a fourth opening 308 sized to mate with a second shaft 316 that carries a second balloon 320 (FIG. 8). During use, the coupler 300 establishes relative positions among the balloons 318, 320, the first set of electrodes 322, and the second set of electrodes 324. Inflation of the balloons 318, 320 compresses tissue region TR surrounded by the balloons 318, 320 and electrodes 322, 324 (FIG. 9).

In other embodiments, instead of having a plurality of electrodes, each of the structures 310, 312 can carry a single electrode. Also, in other embodiments, instead of the rectilinear profile shown, each of the electrodes 322, 324 can have other shapes. In further embodiments, instead of the shafts 314, 316, the openings 306, 308 can be sized to mate with other structures that are used to carry (or are coupled to) the respective balloons 318, 320. Also, in other embodiments, the coupler 300 can have other shapes and configurations as long as the coupler 300 is capable of establishing a relative position between sets of the electrode(s) and balloon(s). For example, in other embodiments, instead of a unitary structure shown, the coupler 300 can include two or more components that may or may not be moveable relative to each other.

Although particular embodiments have been shown and described, it should be understood that the above discussion is not intended to limit the claimed invention. It will be obvious to those skilled in the art that various changes and modifications may be made without departing from the spirit and scope of the present invention. For example, the array 30 of electrodes 26 can be manufactured as a single component. As such, the "array of electrodes" should not be limited to a plurality of separate electrodes, and includes a single structure (e.g., an electrode) having different conductive portions. Also, in any of the embodiments described herein, instead of delivering RF energy, the electrode(s) can be configured to deliver microwave energy, or other forms of energy. Thus, the present invention is intended to cover alternatives, modifications, and equivalents that may fall within the spirit and scope of the present invention as defined by the claims.

What is claimed:

1. A radiofrequency tissue ablation device, comprising:
    an array of elongate electrodes carried by a structure and configured to be deployed in a vascularized tissue region containing blood vessels, the array of elongate electrodes configured to deliver radiofrequency ablative energy to a tissue ablation region defined by the electrode array;
    an inflatable balloon carried by a shaft and configured to be deployed in the vascularized tissue region containing blood vessels; and
    a coupler securing the balloon relative to the array of elongate electrodes, the coupler comprising a first opening dimensioned to receive the shaft and a plurality of secondary openings dimensioned to receive the structure, the plurality of openings configured to alter the distance between the inflatable balloon and the array of elongate electrodes, wherein the balloon, when inflated, is configured to apply a force to vascularized tissue region located in the tissue ablation region so as to reduce blood flow in the vascularized tissue region.

2. The ablation device of claim 1, wherein the coupler is detachably secured to the shaft.

3. The ablation device of claim 1, wherein the coupler is detachably secured to the structure.

4. The ablation device of claim 1, wherein the coupler is detachably secured to the shaft and the structure.

5. The ablation device of claim 1, wherein at least a portion of the balloon is electrically conductive.

6. The ablation device of claim 5, further comprising a generator operatively coupled to one or both of the elongate electrodes and the electrically conductive portion of the balloon.

7. The ablation device of claim 6, wherein the electrode array and the balloon form a bipolar tissue ablation configuration.

8. The ablation device of claim 1, wherein the balloon, when inflated, defines in part the tissue ablation region.

9. A radiofrequency tissue ablation device, comprising:
    an array of elongate electrodes carried by a structure and configured to be deployed in a vascularized tissue region containing blood vessels, the array of elongate electrodes configured to deliver radiofrequency ablative energy to a tissue ablation region defined by the electrode array;
    an inflatable balloon carried by a shaft and configured to be deployed in the vascularized tissue region containing blood vessels; and
    a coupler comprising a first portion having a first opening dimensioned to receive the structure and a second portion having a second opening dimensioned to receive the shaft, the second portion moveable with respect to the first portion to alter the distance between the inflatable balloon and the array of elongate electrodes, the coupler further comprising a securing device configured to secure the first portion relative to the second portion.

10. The ablation device of claim 9, wherein the balloon, when inflated, is configured to apply a force to vascularized tissue region located in the tissue ablation region so as to reduce blood flow in the vascularized tissue region.

11. The ablation device of claim 9, wherein the securing device comprises a screw.

12. The ablation device of claim 9, wherein the first portion of the coupler is detachably secured to the structure.

13. The ablation device of claim 9, wherein the second portion of the coupler is detachably secured to the shaft.

14. The ablation device of claim 9, wherein the first portion of the coupler is permanently secured to the structure.

15. The ablation device of claim 9, wherein the second portion of the coupler is permanently secured to the shaft.

* * * * *